United States Patent
Van Wiemeersch et al.

(10) Patent No.: US 9,457,816 B2
(45) Date of Patent: Oct. 4, 2016

(54) CONTROLLING ACCESS TO AN IN-VEHICLE HUMAN-MACHINE INTERFACE

(71) Applicant: Ford Global Technologies, LLC, Dearborn, MI (US)

(72) Inventors: Adam Leonard Van Wiemeersch, Novi, MI (US); John Robert Van Wiemeersch, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 64 days.

(21) Appl. No.: 14/335,981

(22) Filed: Jul. 21, 2014

(65) Prior Publication Data

US 2016/0016473 A1    Jan. 21, 2016

(51) Int. Cl.
| | | |
|---|---|---|
| *B60W 50/12* | (2012.01) |
| *A61B 5/00* | (2006.01) |
| *B60N 2/00* | (2006.01) |
| *H04M 1/60* | (2006.01) |
| *B60K 37/06* | (2006.01) |
| *G01G 19/414* | (2006.01) |
| *A61B 5/0402* | (2006.01) |
| *A61B 5/0245* | (2006.01) |
| *G01C 21/26* | (2006.01) |

(52) U.S. Cl.
CPC ............ *B60W 50/12* (2013.01); *A61B 5/6893* (2013.01); *B60K 37/06* (2013.01); *B60N 2/002* (2013.01); *G01G 19/4142* (2013.01); *H04M 1/6075* (2013.01); *A61B 5/0245* (2013.01); *A61B 5/0402* (2013.01); *A61B 2562/0214* (2013.01); *B60K 2350/901* (2013.01); *B60K 2350/903* (2013.01); *G01C 21/26* (2013.01)

(58) Field of Classification Search
CPC ..... B60W 50/12; B60N 2/002; B60K 37/06; B60K 2350/901; B60K 2350/903; A61B 5/0245; G01G 19/4142; H04M 1/6075
See application file for complete search history.

(56) References Cited

U.S. PATENT DOCUMENTS

| | | | | |
|---|---|---|---|---|
| 6,029,110 A | * | 2/2000 | Zuber | B60K 35/00 701/36 |
| 6,181,996 B1 | * | 1/2001 | Chou | B60K 37/00 701/36 |
| 6,256,558 B1 | | 7/2001 | Sugiura et al. | |
| 6,668,221 B2 | * | 12/2003 | Harter, Jr. | B60K 35/00 701/36 |
| 7,009,488 B2 | * | 3/2006 | Schwartz | B60K 28/04 340/426.24 |
| 7,194,346 B2 | * | 3/2007 | Griffin | B60R 21/01536 701/45 |
| 7,239,947 B2 | * | 7/2007 | Suzuki | G01C 21/3664 701/36 |
| 8,285,453 B2 | * | 10/2012 | Schroeder | G01C 21/3641 340/425.5 |

(Continued)

OTHER PUBLICATIONS

Herrmann et al., Hand-movement-based in-vehicle driver/front-seat passenger discrimination for centre console controls, © Technical University of Berlin, Str. des 17. Juni 135, 10623 Berlin, Germany (9 pages).

*Primary Examiner* — Dale W Hilgendorf (74) *Attorney, Agent, or Firm* — Frank MacKenzie; Bejin Bieneman PLC (57) ABSTRACT

An in-vehicle computer is programmed to determine that a driver's hands are at least one predetermined location in the vehicle, the at least one predetermine location including a location on a steering wheel, determine that a vehicle passenger is in a safe position with respect to a human-machine interface; and provide passenger access to the human-machine interface such that the passenger may access operations of the computer that are inaccessible to the driver.

16 Claims, 4 Drawing Sheets

(56) References Cited

U.S. PATENT DOCUMENTS

| | | | | |
|---|---|---|---|---|
| 8,301,108 B2* | 10/2012 | Naboulsi | ................ | G08B 21/06 455/345 |
| 2008/0071177 A1* | 3/2008 | Yanagidaira | ........... | A61B 5/024 600/483 |
| 2008/0129684 A1 | 6/2008 | Adams et al. | | |
| 2009/0231145 A1* | 9/2009 | Wada | ..................... | B60K 35/00 701/36 |
| 2010/0250044 A1 | 9/2010 | Alasry et al. | | |
| 2010/0297930 A1* | 11/2010 | Harris | .................... | H04K 3/415 455/566 |
| 2011/0224897 A1 | 9/2011 | Tan | | |
| 2014/0274023 A1* | 9/2014 | Rajeevalochana | .... | H04W 4/027 455/418 |
| 2015/0120081 A1* | 4/2015 | Forcke | ................. | B60W 40/08 701/1 |

\* cited by examiner

CONTROLLING ACCESS TO AN IN-VEHICLE HUMAN-MACHINE INTERFACE

BACKGROUND

Vehicles such as automobiles frequently feature an in-vehicle computer that includes at least one human-machine interface (HMI) allowing a vehicle driver or other occupant to interact with the in-vehicle computer in a variety of ways. For example, an in-vehicle computer can allow a user to place and receive telephone calls, receive streaming media such as radio stations or other audio, control various vehicle systems, such as a climate control system, media player, etc., interact with applications on a smart phone or similar device, and or use other applications, such as a navigation application. However, due to safety concerns, access to an in-vehicle display or other HMI may be restricted, e.g., limited or no operations may be made available while a vehicle is in motion to minimize chances of driver distraction. However, vehicle drivers and their passengers can be frustrated by limitations on an HMI, and access to the vehicle computer, that prevent passengers not engaged in driving the vehicle from accessing, and/or performing certain operations via, the HMI.

DETAILED DESCRIPTION

System Overview

Figure 1:
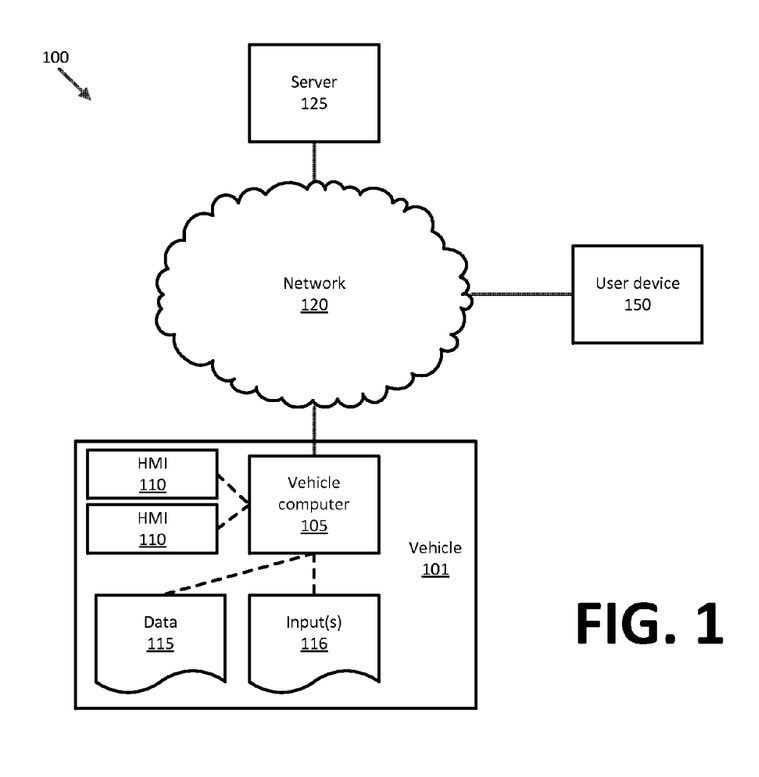
FIG. 1 is a block diagram of an example system for controlling access to a vehicle HMI.

FIG. 1 is a block diagram of an exemplary system 100 for controlling access to one or more HMIs (human machine interfaces) 110 provided for user interaction with a computer 105 in a vehicle 101. The computer 105 may receive various data 115, e.g., from vehicle 101 sensors, controllers, etc., e.g., via a communication bus in the vehicle 101, indicating a state of the vehicle 101, such as whether the vehicle 101 is in motion, a vehicle 101 speed, etc. Further, data 115 may include sensor data indicating a position of a vehicle 101 driver and/or passenger. For example, with reference to FIG. 2, one or more predetermined locations proximate to a vehicle 101 driver, e.g., a vehicle 101 steering wheel 205 and/or a gearshift knob 240, may include sensors 210 such as electrocardiogram (EKG) sensors 210 to provide an indication of whether a driver's hands are on the steering wheel 205. Additionally or alternatively, with reference to FIGS. 2 and 3, a vehicle 101 passenger seat 225 may include sensors 235 for determining whether a passenger's position is suitable for safe operation of the vehicle 101 and/or an HMI 110.

Based on the foregoing and/or other data 115, the computer 105 is programmed to determine whether one or more of the HMI's 110 should be placed in a state restricting driver and passenger access, restricting driver access but allowing passenger access, or allowing driver and passenger access, thereby determining what inputs 116 a driver and/or passenger may provide to the computer 105. Moreover, an HMI 110 could be used to access an application, e.g., a navigation application, a communication application, a media application, etc., provided by a server 125 and/or a user device 150 via a network 120, such access possibly being controlled according to a state of the vehicle 101, a position of a passenger, and/or a status of a driver's hands with respect to a vehicle steering wheel. Yet further, in vehicles 101 that allow an application running on a user device, e.g., smartphone, 150 to control a front seating row HMI 110 display, or second or third seating row HMI 110 displays (e.g., screens of a rear DVD system or the like), such device 150 application control features are typically be disabled if the device 150 application detects the vehicle 101 to be in motion, and/or the vehicle HMI may ignore a command from a smartphone device 150 if the vehicle 101 is in motion. Via use of the sensors 210, e.g., in the steering wheel 205, such remote application features could be allowed if the sensor 210 detects both hands on the steering wheel or in another location, e.g., on a vehicle 101 gearshift knob or the like, thus allowing vehicle 101 passengers full control of device 150 application features even when the vehicle is in motion.

System Elements

A vehicle 101 computer 105 generally includes a processor and a memory, the memory including one or more forms of computer readable media, and storing instructions executable by the processor for performing various operations, including as disclosed herein. The memory of the computer 105 further generally stores data 115 collected from vehicle 101 controllers, sensors, etc. The computer 105 is configured for communications on a controller area network (CAN) bus or the like, and/or other wire or wireless protocols, e.g., BLUETOOTH®, etc., i.e., the computer 105 can communicate via various mechanisms that may be provided in the vehicle 101 and/or other devices such as a user device 150. The computer 105 may also have a connection to an onboard diagnostics connector (OBD II), e.g., according to the J1962 standard. Via the CAN bus, OBD II connector port, and/or other wired or wireless mechanisms, the computer 105 may transmit messages to various devices in a vehicle and/or receive messages from the various devices, e.g., controllers, actuators, sensors, etc. In addition, the computer 105 may be configured for communicating, e.g., with one or more remote servers 125, with the network 120, which, as described below, may include various wired and/or wireless networking technologies, e.g., cellular, Bluetooth, wired and/or wireless packet networks, etc.

An HMI 110 included in or associated with the computer 105 may include a variety of known mechanisms for allowing a user to interface with the computer 105. For example, the HMI 110 could include a microphone, a speaker, text to speech, speech recognition processing capability, etc., for allowing verbal and/or audio interaction with the computer 105, e.g., in the form of an interactive voice response (IVR) system such as is known. Further, the HMI 110 could include a visual display, touchscreen, or the like, such as the display 215 discussed below with respect FIG. 2, and/or other input/output mechanisms.

Data 115 may be obtained from a variety of devices, e.g., cameras, radar, lidar, ultrasonic sensors, accelerometers, weight sensors, position sensors, etc. In a particular example, data 115 may be obtained from electrocardiogram (EKG) sensors 210 and/or position sensors 230, discussed below with reference to FIG. 2. Further for example, various controllers in a vehicle may operate as data collectors 110 to provide data 115 via the CAN bus, e.g., data 115 relating to vehicle speed, acceleration, location, etc., in addition to environmental conditions such mentioned above. Further, sensors or the like, global positioning system (GPS) equipment, etc., could be included in a vehicle and configured to provide data 115 directly to the computer 105, e.g., via a wired or wireless connection.

The network 120 represents one or more mechanisms by which a vehicle computer 105 may communicate with a remote server 125, including to obtain remote data. Accordingly, the network 120 may be one or more of various wired or wireless communication mechanisms, including any desired combination of wired (e.g., cable and fiber) and/or wireless (e.g., cellular, wireless, satellite, microwave, and radio frequency) communication mechanisms and any desired network topology (or topologies when multiple communication mechanisms are utilized). Exemplary communication networks include wireless communication networks (e.g., using BLUETOOTH, IEEE 802.11, etc.), local area networks (LAN) and/or wide area networks (WAN), including the Internet, providing data communication services.

The server 125 may be one or more computer servers, each generally including at least one processor and at least one memory, the memory storing instructions executable by the processor, including instructions for carrying out various of the steps and processes described herein. The server 125 may include or be communicatively coupled to a data store 130 for storing remote data 115.

A user device 150 may be any one of a variety of computing devices including a processor and a memory, as well as communication capabilities. For example, the user device 155 may be a portable computer, tablet computer, a smart phone, etc. that includes capabilities for wireless communications using IEEE 802.11, BLUETOOTH, and/or cellular communications protocols. Further, the user device 150 may use such communications capabilities to communicate via the network 120 and also directly with a vehicle computer 105, e.g., using an in vehicle communications mechanism, e.g., BLUETOOTH. Accordingly, the computer 105 could control access to one or more applications on a device 150 accessed via a computer 105 HMI 110.

Figure 2:
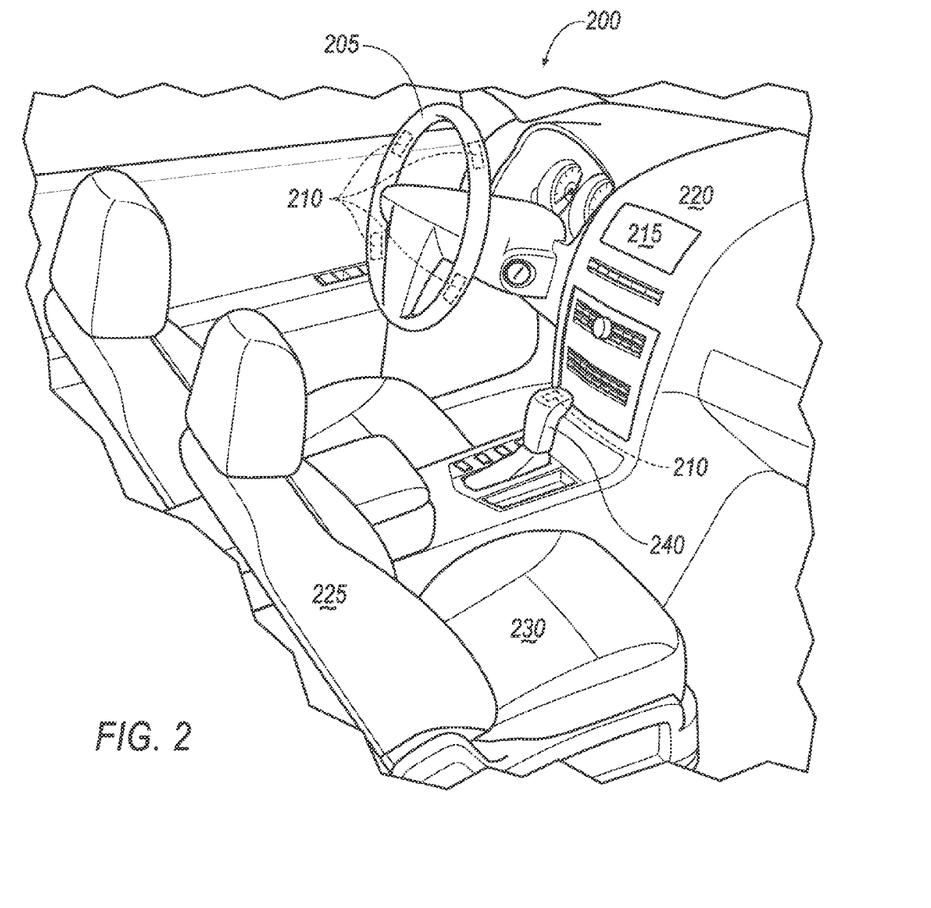
FIG. 2 illustrates example elements in a vehicle for controlling access to a vehicle HMI.
Figure 3:
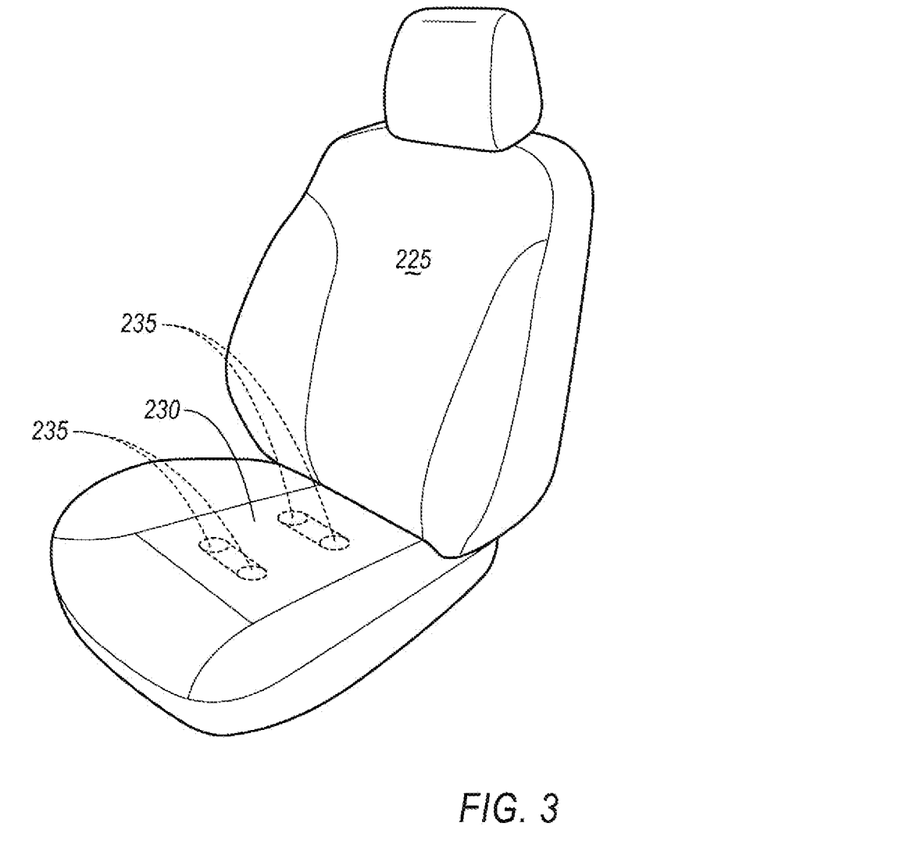
FIG. 3 illustrates an example of a vehicle seat including sensors for detecting a passenger position.

FIG. 2 illustrates example elements of a portion of a passenger compartment 200 in a vehicle 101 for controlling access to a vehicle HMI. FIG. 3 illustrates an example of vehicle seat 225 including sensors 235 for detecting a passenger position. As seen in FIG. 2, a vehicle 101 steering wheel 205 has sensors 210 embedded therein. For example, the sensors 210 may be those such as are known EKG sensors or the like for use in exercise equipment. The sensors 210 may be provided at or below a surface of the steering wheel 205 in a known manner for detecting an EKG signal from contact with a human body part, in this case, hands of a vehicle 101 driver. Further, one or more sensors 210 could be provided in another location or locations on which a driver's hand or hands may rest during safe operation of the vehicle 101, e.g., a gearshift knob 240.

Accordingly, when the sensors 210 detect a human heartbeat, an indication of the heartbeat may be provided to the computer 105, e.g., via communications mechanisms such as discussed above. Further, the sensors 210 may indicate a particular location of a sensor 210 on the steering wheel 205 where the human heartbeat is detected. Accordingly, the sensors 210 may collectively provide information to the computer 105 for determining whether no, one, or both driver hands are firmly gripping the steering wheel 205 and/or gearshift knob 240, etc.

The sensors 210 shown in FIG. 2 could be combined with or replaced by other sensors. For example, capacitive sensors or the like such as are known could be included on the steering wheel 205, knob 240, etc. In one implementation, capacitive sensors could be provided on a backside of the steering wheel 205 to supplement the EKG sensors 210, whereby the computer 105 could use data 115 from the capacitive sensors in addition to EKG data 115 to determine whether a driver's hands were firmly on the steering wheel 205, or whether the driver's hands were only loosely or partially on the steering wheel 205. For example, if a driver rested his or her palms on sensors 210, capacitive sensors on a back side of the steering wheel 205 could provide data 115 in addition to EKG data 115 indicating to the computer 105 that the driver's hands were not firmly on the steering wheel 205. Likewise, such arrangement of EKG sensors 210 and/or other sensors on a front and a back and/or surrounding a steering wheel 205 could detect mechanisms used by a driver to defeat restrictions on an HMI 110, e.g., a coupling strap or the like from a driver's hand to an EKG sensor 210.

In a further additional or alternative embodiment, a set of sensors 210 could be included in an HMI 110 the screen and a passenger door handle such that measurements of a vehicle 101 driver are not even involved. For example, if the passenger has a right hand on the a passenger interior door grab handle (e.g., a handle used to pull the door shut) and a left hand is detected on an HMI 110 touch screen, then an EKG pattern from these two sensors 210 could be reference points to allow otherwise restricted features to be executed from the HMI 110 touch screen.

As mentioned above, a passenger seat 225 may include, e.g., embedded in a seat surface 230, one or more sensors 235 for determining a position of a passenger in the seat 225. For example, the sensors 235 may be weight sensors or the like, and/or may be included as part of an occupant classification system (OCS) such as is known for determining a passenger size and/or weight for a vehicle safety system, e.g., a system that deploys airbags or the like. Further, data 115 concerning a passenger presence and/or position may be provided by other mechanisms, e.g., a camera could be included in a vehicle console 220, the vehicle console 220 generally further including a display 215. Accordingly, sensors 235, seen in FIG. 3, and/or other mechanisms such as a camera or cameras can be used to determine whether a passenger is leaning unsafely forward toward a vehicle 101 dash, the console 220 and/or the display 215.

Exemplary Process Flow

Figure 4:
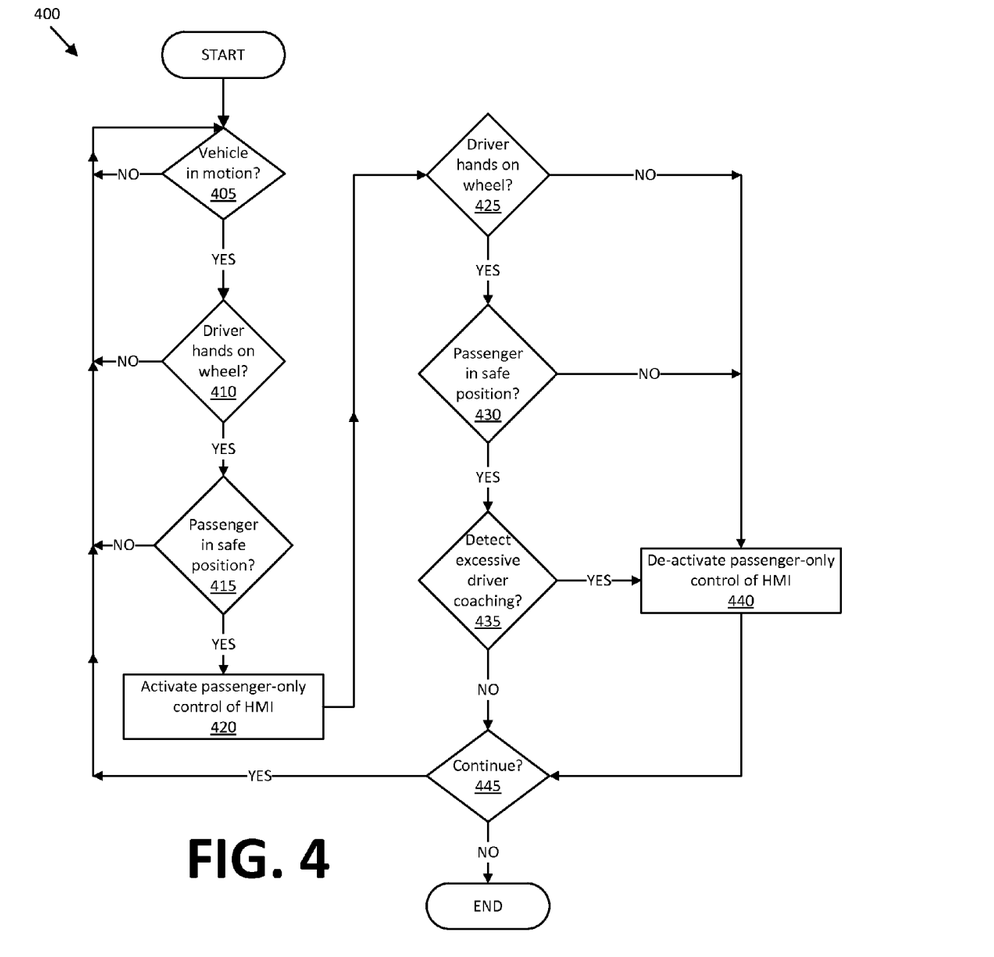
FIG. 4 is a diagram of an exemplary process for controlling access to a vehicle HMI.

FIG. 4 is a diagram of an exemplary process for controlling access to a vehicle 101 HMI. The process 400 begins in a block 405, wherein the computer 105 determines whether the vehicle 101 is in motion. For example, via a CAN bus or the like, the computer 105 may receive information indicating a vehicle speed, direction, etc. If the vehicle 101 is in motion, then a block 410 is executed next. Otherwise, the process 400 continues in the block 405 (or, although not shown in FIG. 4, it is to be understood that the process 400 may end if the computer 105 and/or the vehicle 101 are powered off).

Next, in a block 410, the computer 105, using data 115 from EKG sensors 210, determines whether the driver's hands can be detected in predetermined locations identified as being consistent with safe operation of the vehicle 101, e.g., both driver hands are on the steering wheel 205, a first hand is on the steering wheel 205 and a second hand is on the gearshift knob 240. Further, in some implementations, sensors 210 and/or other sensors may be arranged as described above to provide data 115 from which the computer 105 can determine whether a driver's hands are firmly on a steering wheel 205 and/or whether all, i.e., palms and fingers, of a driver's hands are on the steering wheel 205, knob 240, etc., whereby, if not, a negative determination may be made in the block 410 even if a driver's hands are partly or loosely on the steering wheel 205, knob 240, etc. In any event, a negative determination in the block 410 returns the process 400 to the block 405. An affirmative determination results in the process 400 proceeding to a block 415.

Note that, when a sensor 210 is included in a gearshift knob 240, there is a risk that a vehicle 101 driver could attempt to circumvent the system 100, e.g., by resting a hand or wrist on the knob 240, but then extending fingers to manipulate the HMI 110 display 215, or using a conductive strap or the like to connect the driver's hand to the knob 240 while allowing the driver's hand to roam to operate the display 215. To account for this possibility, the display 215, likely a capacitive touch screen or the like, could include or operate as an sensor 210. An EKG sensor 210 signal detected from a gearshift knob 240 could be compared to an EKG signal from the display 215. If these signals substantially match, then the determination of the block 410 should generally be negative.

Yet further in the block 410, the computer 105 may be programmed to perform validations of sensor 210 signals. For example, the computer 105 could be programmed to compare a received EKG sensor 210 signal with a stored pattern or patterns representing an EKG signal expected form a human being, e.g., including variations, irregularities, etc. that a human-generated signal likely will include, as opposed to a signal from a signal generator. Further, a memory of the computer 105 could store a pattern or patterns associated with a specific driver, e.g., based on sensor 210 data received over time and/or stored from an external source, and compare such stored data to data being received form sensors 210. In any event, if the computer 205 determines that received sensor 210 data does not match a predetermined pattern or range of patterns, the determination of the block 410 may be negative.

In the block 415, the computer 105 determines whether a front row passenger is in a safe position. For example, sensors 235 and/or other sensors, e.g., a camera or cameras as discussed above, may be used to determine whether a front row passenger in the seat 225 is a sufficient distance from a vehicle dashboard and/or the console 220 for safe operation of the vehicle 101 and/or operation of an HMI 110, e.g., the display 215. If the passenger is in a safe position, then a block 420 is executed next. Otherwise, the process 400 returns to the block 405.

In the block 420, the computer 105 activates a passenger-only portion of at least one HMI 110 in the vehicle 101. As mentioned above, the computer 105 may be programmed to provide different levels of access to one or more HMI's 110. For example, when vehicle motion is detected as described above with respect to the block 405, the computer 105 provides a restricted level of access for both the vehicle 101 driver and any passengers. That is, a first set of operations of the computer 105 and/or an HMI 110 may be permitted, e.g., adjusting a volume of audio media, receiving a telephone call, etc. However, in a driver and passenger restricted mode, a second set of operations may be prevented, e.g., accessing a navigation system, accessing a webpage, sending or receiving a text message, etc. In the block 420, the computer 105 may activate a passenger-only portion of an HMI 110, whereby a vehicle 101 driver may still be permitted a limited first set of operations via the HMI, but the vehicle 101 passenger may be permitted a second set of operations via the HMI in addition to the limited first set of operations. Further, the computer 105 could allow an application running on a device 150, e.g., a passenger smartphone, to perform operations that would otherwise be prohibited, as mentioned above.

Following the block 420, in a block 425, the computer 105 determines whether a driver's hands are on, surround, and/or are firmly on, a steering wheel 205, knob 240, etc. The block 425 is generally performed in the manner discussed with respect to the block 410. In some implementations of the process 400, the block 425 is performed on a predetermined periodic basis, e.g., every 5 seconds, every 10 seconds, every 30 seconds, etc. That is, the computer 105 may be programmed to take into account legitimate reasons why a driver's hands may leave a steering wheel 205 for very short durations. For example, a driver may need to activate a vehicle 101 control such as a turn signal, a climate control, a light, a gearshift, etc. An affirmative determination in the block 425 results in the process 400 proceeding to a block 430; a negative determination results in the process 400 proceeding to a block 440.

In the block 430, the computer 105 determines whether a passenger is in a safe position for use of an HMI 110. The block 430 is generally performed in the manner discussed with respect to the block 415. An affirmative determination in the block 430 results in the process 400 proceeding to a block 435; a negative determination results in the process 400 proceeding to a block 440.

In the block 435, the computer 105 determines whether a passenger operating the HMI to which access or expanded access was provided in the block 420 is receiving excessive coaching from a vehicle 101 driver. That is, the driver could be viewing the display 215, listening to audio output from an HMI 110, etc., and providing comments and/or instructions to a passenger for operation of the HMI 110. Such driver activity may pose risks to vehicle 101 safety, e.g., may indicate driver distraction similar to driver distraction from actually operating an HMI 110 while driving. Driver coaching may be detected by an HMI 110 equipped for speech recognition. For example, a tone of a driver's voice, a volume of speech, a number of words spoken, and/or particular words spoken that correlate to options being presented via the display 215, e.g., touch screen, e.g., relating to commands or the like for the HMI 110, could indicate excessive driver coaching. Additionally or alternatively, driver coaching could be determined by using a camera or the like to identify a driver gaze directed toward the display 215 or other HMI element for an excessive period of time, e.g., 3 seconds, 5 seconds, 10 seconds, etc. If excessive driver coaching is detected, then the block 440 is executed next with an option to provide the occupants with a display notification or voice notification the feature has been suspended due to coaching. Otherwise, the process 400 proceeds to a block 445.

In the block 440, which may follow any of the block 425, 430, 435, the computer 105 deactivates passenger-only operations of the HMI 110 that were activated in the block 420. Following the block 440, the process 400 proceeds to the block 445.

In the block 445, the computer 105 determines whether the process 400 should continue. For example, if a vehicle is not in motion, e.g., a "park" setting of the vehicle 101 transmission is engaged, then the process 400 could be ended. Upon ending the process 400, the computer 105 may restore all levels of access to one or more HMI's 110 to the vehicle 101 driver and/or any passengers, whereas while the vehicle 101 is in motion, the computer 105 may restrict access for the vehicle 101 driver, as well as for a passenger depending on a passenger position and/or other factors such as described above.

CONCLUSION

Computing devices such as those discussed herein generally each include instructions executable by one or more computing devices such as those identified above, and for carrying out blocks or steps of processes described above. For example, process blocks discussed above may be embodied as computer-executable instructions.

Computer-executable instructions may be compiled or interpreted from computer programs created using a variety of programming languages and/or technologies, including, without limitation, and either alone or in combination, JAVA™, C, C++, VISUAL BASIC®, JAVA SCRIPT™, PERL®, HTML, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media. A file in a computing device is generally a collection of data stored on a computer readable medium, such as a storage medium, a random access memory, etc.

A computer-readable medium includes any medium that participates in providing data (e.g., instructions), which may be read by a computer. Such a medium may take many forms, including, but not limited to, non-volatile media, volatile media, etc. Non-volatile media include, for example, optical or magnetic disks and other persistent memory. Volatile media include dynamic random access memory (DRAM), which typically constitutes a main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

In the drawings, the same reference numbers indicate the same elements. Further, some or all of these elements could be changed. With regard to the media, processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A system for a vehicle, comprising a computer comprising a processor and a memory, programmed to:
   determine that a driver's hands are on a steering wheel;
   detect human speech according to speech recognition processing included in a human machine interface (HMI) to determine that the driver is coaching a passenger concerning operating the HMI; and
   disable all occupant access to the HMI based on identifying the coaching.

2. The system of claim 1, further comprising at least one electrocardiogram sensor, the computer being further programmed to associate the data from the electrocardiogram sensor with the driver of the vehicle.

3. The system of claim 1, further comprising at least one electrocardiogram sensor, the computer being further programmed to perform a validation to determine whether signals from the at least one electrocardiogram sensor represent a human heartbeat.

4. The system of claim 1, further comprising a sensor in a display of the human machine interface arranged to provide data concerning a location of at least one of the driver's hands on the steering wheel.

5. The system of claim 1, wherein the human-machine interface includes at least one of a visual display, a touchscreen, a speaker, and a microphone.

6. The system of claim 1, further comprising a plurality of sensors arranged to provide inputs for determining whether the passenger is in a safe position.

7. The system of claim 6, wherein the sensors include at least one of a weight sensor, a camera, and a sensor included in an occupant classification system (OCS).

8. The system of claim 1, further comprising at least two sensors arrangeable in the steering wheel, wherein to determine that the driver's hands are on the steering wheel includes to determine that palms and fingers of both of the driver's hands are on the steering wheel.

9. A method, comprising:
   determining that a driver's hands are on a steering wheel of a vehicle;
   detecting human speech according to speech recognition processing included in a human machine interface (HMI) to determine that the driver is coaching a passenger concerning operating the HMI; and
   disabling all occupant access to the HMI based on identifying the coaching.

10. The method of claim 9, further comprising associating the data from at least one electrocardiogram sensor with the driver of the vehicle.

11. The method of claim 9, further comprising performing a validation of data from at least one electrocardiogram sensor to determine whether signals from the at least one electrocardiogram sensor represent a human heartbeat.

12. The method of claim 9, further comprising receiving data from a sensor in a display of the human machine interface to determine a location of at least one of the driver's hands on the steering wheel.

13. The method of claim 9, wherein the human-machine interface includes at least one of a visual display, a touchscreen, a speaker, and a microphone.

14. The method of claim 9, further comprising receiving inputs from a plurality of sensors to determine whether the passenger is in a safe position.

15. The method of claim 14, wherein the sensors include at least one of a weight sensor, a camera, and a sensor included in an occupant classification system (OCS).

16. The method of claim 9, wherein determining that the driver's hands are on the steering wheel includes determining that palms and fingers of both of the driver's hands are on the steering wheel.

\* \* \* \* \*